United States Patent [19]

Lee et al.

[11] Patent Number: 5,491,170
[45] Date of Patent: Feb. 13, 1996

[54] β-CARBOXY SULFONAMIDE ACAT INHIBITORS

[75] Inventors: Helen T. Lee, Ann Arbor; Joseph A. Picard, Canton; Drago R. Sliskovic, Ypsilanti, all of Mich.

[73] Assignee: Warner-Lambert Company, Morris Plains, N.J.

[21] Appl. No.: 359,115

[22] Filed: Dec. 19, 1994

[51] Int. Cl.⁶ .................... A61K 31/19; A61K 31/215; C07C 311/25

[52] U.S. Cl. .................... 514/538; 514/513; 514/529; 514/510; 514/550; 514/562; 514/601; 514/603; 514/605; 558/252; 560/10; 560/17; 560/125; 560/139; 560/145; 560/149; 560/150; 562/427; 562/430; 562/507; 562/556; 564/80; 564/86; 564/95

[58] Field of Search .................... 558/252; 560/10, 560/12, 125, 139, 145, 149, 150; 562/427, 430, 567, 556; 564/80, 86, 95; 514/513, 529, 510, 538, 550, 562, 601, 603, 605

[56] References Cited

U.S. PATENT DOCUMENTS

| | | | |
|---|---|---|---|
| 2,998,420 | 8/1961 | Weinstock | 260/251.5 |
| 3,303,191 | 2/1967 | Loev | 260/243 |
| 4,309,559 | 1/1982 | Cliff | 560/12 |
| 5,130,119 | 7/1992 | Blaszkiewicz et al. | 424/9 |
| 5,239,082 | 8/1993 | Lee et al. | 548/252 |
| 5,254,715 | 10/1993 | Picard et al. | 560/13 |
| 5,366,987 | 11/1994 | Lee et al. | 514/378 |

OTHER PUBLICATIONS

Rossi et al., Chemical Abstracts, vol. 65 (1966) 10582h.
Bruno et al., Chemical Abstracts, vol. 59 (1963) 5068d.
Hypoglycemic Sulfamylureas. III, vol. 8, Nov. 1965, McFarland et al., pp. 781–784.
*Bulletin de la Société Chimique de France*, No. 1, 1988, Baltas et al., pp. 79–87.

*Primary Examiner*—Richard L. Raymond
*Attorney, Agent, or Firm*—Charles W. Ashbrook

[57] ABSTRACT

β-Carboxy sulfonyl compounds of the formula

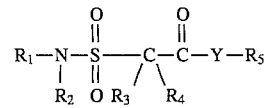

wherein $R_1$ is aryl, $R_3$ is hydrogen or alkyl, $R_3$ and $R_4$ are hydrogen or alkyl, Y is —O—, —S—, or —NR$_2$—, and $R_5$ is alkyl or aryl are potent inhibitors of the enzyme acyl CoA:cholesterol acyltransferase (ACAT) and are thus useful for treating hypercholesterolemia and atherosclerosis.

40 Claims, No Drawings

β-CARBOXY SULFONAMIDE ACAT INHIBITORS

BACKGROUND OF THE INVENTION

This invention provides new chemical compounds characterized as being β-carboxy sulfonamides. The compounds inhibit acyl-CoA: cholesterol acyltransferase (ACAT), the enzyme responsible for the esterification of dietary cholesterol. Such agents thus decrease the absorption of dietary cholesterol and therefore provide a therapy for individuals with hypercholesterolemia and atherosclerosis.

High levels of cholesterol have been associated with heightened risk for development of several disease states, most notably coronary heart disease. A great deal of effort has been devoted to finding ways to lower cholesterol levels in biological systems. The approach of lowering cholesterol intake by modifying diet has met with only limited success. The ACAT enzyme is known to catalyze the esterification of dietary cholesterol, and has been implicated in several aspects of the atherosclerotic process in animals. One approach to lowering cholesterol then is to inhibit the ACAT enzyme. While several ACAT inhibitors have been identified (see for example EP 0570245), the need continues to identify and develop new ACAT inhibitors having improved therapeutic properties.

An object of this invention is therefore to provide a new series of compounds which are β-carboxy sulfonamide derivatives and which have demonstrated excellent ACAT inhibitory properties. Another object is to provide pharmaceutical formulations comprising the sulfonamides and a carrier or excipient, and a method for inhibiting the ACAT enzyme by administering a compound of the invention.

SUMMARY OF THE INVENTION

This invention concerns new compounds which are β-carboxy sulfonamides and which inhibit the ACAT enzyme. The compounds of the invention have the Formula I

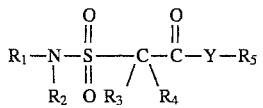

wherein $R_1$ is selected from
(a) phenyl which is unsubstituted or is substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$, wherein m is 0 or 1, and each of $R_x$ and $R_y$ is independently hydrogen or $C_1$–$C_4$ alkyl;
(b) 1- or 2-naphthyl which is unsubstituted or substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$, wherein m is 0 or 1, and each of $R_x$ and $R_y$ is independently hydrogen or $C_1$–$C_4$ alkyl;
(c) the group

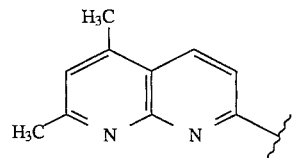

(d) the group

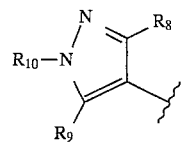

wherein $R_8$ and $R_9$ independently are $C_1$–$C_4$ alkyl or phenyl, and $R_{10}$ is a straight or branched hydrocarbon group having from 1 to 18 carbon atoms which is saturated or is unsaturated containing one double bond or two nonadjacent double bonds; phenyl; phenyl substituted with from 1 to 3 substituents selected from
$C_1$–$C_4$ alkyl,
$C_1$–$C_4$ alkoxy,
hydroxy,
halo,
nitro,
cyano,
trifluoromethyl,
—COOH,
—COOalkyl wherein alkyl has from 1 to 4 carbon atoms and is straight or branched,
—$(CH_2)_m NR_x R_y$, wherein m, $R_x$, and $R_y$ are as defined above; or
a heterocyclic group selected from 2-, 3-, or 4-pyridyl, 2-, 4-, or 5-pyrimidinyl, 2-, or 3-pyrazinyl, 2-, 3-, 4-, 5-, 6-, 7-, or 8-quinolinyl, 3- or 4-pyridazinyl, and the N-oxides thereof;
(e) the group

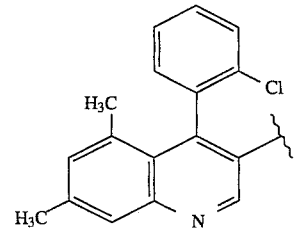

(f) a straight or branched hydrocarbon group having from 1 to 18 carbon atoms which is saturated or is unsaturated containing one double bond or two nonadjacent double bonds;

(g) a cycloalkyl group having from 3 to 10 carbon atoms;

(h) the group

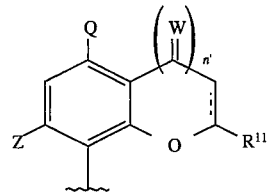

wherein - - - denotes a single or double bond;

Q and Z are each independently hydrogen, $C_1$–$C_4$ alkyl, $C_1$–$C_4$ alkoxy, or halo;

W is oxygen or two hydrogen atoms;

$R^{11}$ is hydrogen or $C_1$–$C_4$ alkyl, and n' is 0 or 1;

(i) is selected from the group

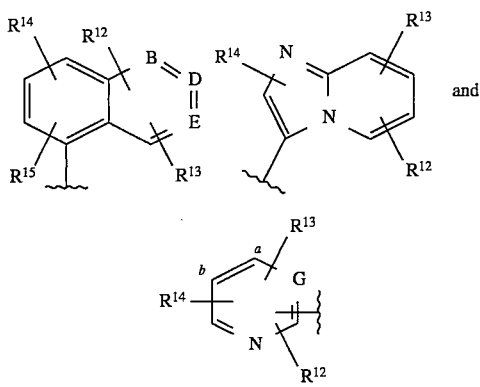

wherein $R^{12}$, $R^{13}$, $R^{14}$, and $R^{15}$ are each independently hydrogen, halo, $C_1$–$C_4$ alkyl, $C_1$–$C_4$ alkoxy, $C_1$–$C_4$ alkylthio, cycloalkylthio of 5 to 7 carbon atoms, phenylalkylthio in which alkyl is 1 to 4 carbon atoms, substituted phenylthio, heteroarylthio, or heteroaryloxy;

and B, D, E, and G are nitrogen or carbon where one or more of B, D, and E is nitrogen;

with the proviso that when G=N, the group is attached to the nitrogen atom of Formula I at the four or five position of the pyrimidine ring (a and b); or (j) a 5- or 6-membered monocyclic or fused bicyclic heterocycle containing from 1 to 4 heteroatoms selected from nitrogen, oxygen, and sulfur;

$R_2$ is hydrogen or a group defined as for $R_1$;

$R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, phenyl, 1- or 2- naphthyl, or phenyl or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl, or $R_3$ and $R_4$ taken together with the carbon to which they are attached complete a $C_3$–$C_8$ carbocyclic ring;

Y is —O—, —S—, or —$NR_2$'— wherein $R_2$' is $R_2$ as defined above;

$R_5$ is $R_6$, $C_1$–$C_{20}$ alkyl, $C_2$–$C_{20}$ alkenyl, $C_2$–$C_{20}$ alkynyl and alkyl, alkenyl and alkenyl substituted with one or two groups defined by $R_6$, where $R_6$ is hydrogen, $C_3$–$C_6$ cycloalkyl, phenyl, 1- or 2- naphthyl, and phenyl and naphthyl substituted with from 1 to 3 substituents selected from:

$C_1$–$C_4$ alkyl, $C_1$–$C_4$ alkoxy, $C_1$–$C_4$ alkylthio, phenyl, hydroxy, halo, nitro, cyano, trifluoromethyl,

—COOH,

—COOalkyl wherein alkyl has from 1 to 4 carbon atoms and which is straight or branched, —$(CH_2)_mNR_xR_y$, wherein m is 0 or 1, and each of $R_x$ and $R_y$ is hydrogen or a straight chain alkyl group having 1 to 4 carbon atoms; and $R_6$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with amino, halo, nitro, hydroxy, cyano, trifluoromethyl, or an alkyl group having from 1 to 20 carbon atoms and the N-oxides thereof.

Preferred compounds of the invention have the Formula II

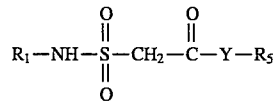

wherein $R_1$, Y, and $R_5$ are as defined above. Further preferred are those of the above formula in which Y is —O—, —S—, or —NH—, and especially where Y is S. Additionally preferred are compounds of Formula II wherein $R_1$ is phenyl or substituted phenyl, Y is —O— or —NH—, and $R_5$ is $C_6$–$C_{20}$ alkyl, phenyl, or substituted phenyl.

Particularly preferred compounds have Formula II wherein:

A. $R_1$ is phenyl or phenyl substituted with 1 or 2 $C_1$–$C_4$ alkyl groups;

A(1) Y is NH and $R_5$ is $C_6$–$C_{20}$ alkyl;

A(2) Y is NH and $R_5$ is phenyl or phenyl substituted with 1 or 2 $C_1$–$C_4$ alkyl or $C_1$–$C_4$ alkoxy groups;

A(3) Y is NH and $R_5$ is pyridyl or pyridyl substituted with 1 or 2 $C_1$–$C_4$ alkyl groups;

A(4) Y is S and $R_5$ is $C_6$–$C_{20}$ alkyl;

A(5) Y is O and $R_5$ is $C_6$–$C_{20}$ alkyl;

A(6) Y is O and $R_5$ is phenyl or phenyl substituted with 1 or 2 $C_1$–$C_4$ alkyl groups;

A(7) Y is NH and $R_5$ is tetrazolyl or tetrazolyl substituted with a $C_6$–$C_{20}$ alkyl group;

B. $R_1$ is phenyl substituted with 1, 2, or $C_1$–$C_4$ alkoxy groups;

B(1) Y is NH and $R_5$ is phenyl or phenyl substituted with 1, 2, or 3 $C_1$–$C_4$ alkoxy groups;

B(2) Y is NH and $R_5$ is $C_6$–$C_{20}$ alkyl;

B(3) Y is S and $R_5$ is $C_6$–$C_{20}$ alkyl;

B(4) Y is O and $R_5$ is $C_6$–$C_{20}$ alkyl;

B(5) Y is O and $R_5$ is phenyl or phenyl substituted with 1, 2, or 3 $C_1$–$C_4$ alkoxy groups;

C. $R_1$ is 1- or 2-naphthyl or 1- or 2-naphthyl substituted with 1, 2, or 3 groups selected from $C_1$–$C_4$ alkyl or $C_1$–$C_4$ alkoxy;

C(1) Y is NH and $R_5$ is $C_6$–$C_{20}$ alkyl, phenyl, or phenyl substituted with 1, 2, or 3 groups selected from $C_1$–$C_4$ alkyl or $C_1$–$C_4$ alkoxy;

C(2) Y is S and $R_5$ is $C_6$–$C_{20}$ alkyl;

C(3) Y is O and $R_5$ is $C_6$–$C_{20}$ alkyl, phenyl, tetrazolyl, or phenyl substituted with 1, 2, or 3 $C_1$–$C_4$ alkyl groups;

C(4) Y is O and $R_5$ is hydrogen;

D. $R_1$ is $C_1$–$C_{20}$ alkyl;

D(1) Y is O and $R_5$ is phenyl or phenyl substituted with 1 or 2 $C_1$–$C_4$ alkyl groups;

D(2) Y is S and $R_5$ $C_6$–$C_{20}$ alkyl;

E. $R_1$ is pyridyl or pyridyl substituted with 1 or 2 $C_1$–$C_4$ alkyl groups;

E(1) Y is O or S and $R_5$ $C_6$–$C_{20}$ alkyl;

F. $R_1$ is 4,6-dialkylpyridin-5-yl;

F(1) Y is NH and $R_5$ $C_6$–$C_{20}$ alkyl;

F(2) Y is S and $R_5$ is phenyl or phenyl substituted with 1, 2, or 3 $C_1$–$C_4$ alkyl groups;

G. $R_1$ is 4-(2-chlorophenyl)-5,7-dimethylquinolin-2-yl;

G(1) Y is O and $R_5$ is $C_6$–$C_{20}$ alkyl;

G(2) Y is NH and $R_5$ is phenyl or phenyl substituted with 1, 2, or 3 $C_1$–$C_4$ alkoxy groups;

G(3) Y is S and $R_5$ is $C_2$–$C_{20}$ alkenyl;

The most preferred compounds of the invention are defined by Formula II when $R_1$ is phenyl or substituted phenyl, Y is sulfur and $R_5$ is $C_6$–$C_{20}$ alkyl.

Also provided by this invention are pharmaceutical formulations comprising a compound of Formula I together with a pharmaceutically acceptable excipient, carrier, or diluent. Preferred formulations are those having a compound of Formula II or any of the preferred compounds of A–G as the active ingredient. The invention also provides a method of treating hypercholesterolemia, atherosclerosis, and inhibiting the ACAT enzyme, comprising administering to a subject an effective amount of a compound of Formula I to treat such conditions and to inhibit such enzyme.

DETAILED DESCRIPTION

Pharmaceutically acceptable salts of the compounds of Formula I are also included as a part of the present invention. Suitable acids for forming salts of the compounds of Formula I containing a basic group include, but are not necessarily limited to acetic, benzoic, benzenesulfonic, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. Additional acids for use to form acid salts of the compounds of Formula I include, but are not necessarily limited to, those acids found in Tables 3 and 4 of Grant & Hackh's Chemical Dictionary, Fifth Edition, 1987:11–13. The acid addition salts are formed by procedures well known in the art.

Certain compounds of the present invention may also exist in different isomeric forms, specifically stereoisomeric forms, by virtue of the presence of asymmetric centers in the compound. The present invention contemplates all stereoisomers that may be obtained, if desired, by methods known in the art as, for example, the separation of stereoisomers by chiral chromatographic columns.

Further, the compounds of this invention may exist in unsolvated as well as solvated forms with pharmaceutically acceptable solvents such as water, ethanol, and the like. In general, the solvated forms are considered equivalent to the unsolvated forms for the purposes of this invention.

In Formula I, $R_5$ can be $C_1$–$C_{20}$ alkyl, $C_2$–$C_{20}$ alkenyl, or $C_2$–$C_{20}$ alkynyl. Each of these groups can have one or two groups defined by $R_6$ attached, for example a substituted or unsubstituted phenyl, or a substituted or unsubstituted naphthyl, or a cycloalkyl such as cyclopropyl can be attached to the carbon chain. Illustrative examples of straight or branched saturated hydrocarbon chains having from 1 to 20 carbon atoms include methyl, ethyl, 2-cyclobutyl-2-phenylethyl, n-propyl, isopropyl, n-butyl, iso-butyl, tert-butyl, n-pentyl, 5-phenylpentyl, 2-cyclopropyl- 5-phenylpentyl, isopentyl, n-hexyl, n-heptyl, n-octyl, n-undecyl, n-dodecyl, n-hexadecyl, 2,2-dimethyldodecyl, 2-tetradecyl, and n-octadecyl groups.

Illustrative examples of straight or branched hydrocarbon alkenyl chains having from 2 to 20 carbon atoms and having one double bond or two nonadjacent double bonds include ethenyl, 2-propenyl, 2-butenyl, 4-cyclobutyl-2-butenyl, 3-pentenyl, 2-octenyl, 5-nonenyl, 4-undecenyl, 5-heptadecenyl, 3-octadecenyl, 9-octadecenyl, 9-phenyl-9-octadecenyl, 2,2-dimethyl- 11-eicosenyl, 9,12-octadecadienyl, and hexadecenyl. Typical alkynyl groups are those having from 2 to 20 carbon atoms with one triple bond or two monoadjacent triple bonds and include 2-octynyl, 5-hepta-3-decynyl, and 4-phenyl-2-butynyl.

$R_1$ in Formula I includes phenyl substituted with 1, 2, or 3 groups such as $C_1$–$C_4$ alkyl, $C_1$–$C_4$ alkoxy and $C_1$–$C_4$ alkylthio. Straight or branched $C_1$–$C_4$ alkyl groups include methyl and isopropyl. Straight or branched alkoxy groups having 1 to 4 carbon atoms include methoxy, ethoxy, n-propoxy, n-butoxy, and isopropoxy. $C_1$–$C_4$ alkylthio includes groups such as methylthio, ethylthio, isopropylthio, and the like.

Cycloalkyl groups having from 3 to 10 carbon atoms which $R_1$ and $R_4$ may represent include cyclopropyl, cyclobutyl, cyclopentyl, cyclohexyl, cycloheptyl, and cyclooctyl.

Halo is fluoro, chloro, bromo, or iodo, but preferably bromo and chloro.

A 5- or 6-membered monocyclic or fused bicyclic heterocycle is a monocyclic or fused bicyclic aromatic ring containing at least one to four heteroatoms in at least one ring, such as nitrogen, oxygen, or sulfur, or a combination thereof. Such a heterocyclic group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, benzothiazolyl, indolyl, quinolinyl, isoquinolinyl, or N-oxides of heterocycles containing a nitrogen atom. More specifically, such a heterocycle may be a 2- or 3-thienyl; 2- or 3- furanyl; 2-, 3-, or 4-pyridyl or 2-, 3-, or 4-pyridinyl-N-oxide; 2-, 4-, or 5-pyrimidinyl; 3- or 4-pyridazinyl; 2-pyrazinyl; 2-pyrazinyl-N-oxide; 2- or 3-pyrrolyl; 3-, 4-, or 5-pyrazolyl; 2-, 4-, or 5-thiazolyl; 3-, 4-, or 5-isoxazolyl; 2-, 4-, or 5-oxazolyl; 3-, 4-, or 5-isothiazolyl; 5- tetrazolyl; 3- or 5- (1,2,4) -triazolyl; 4- or 5-(1,2,3)-triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; or 2-, 3-, 4-, 5-, 6-, or 7-benzothienyl.

A preferred embodiment of this invention includes compounds having the formula

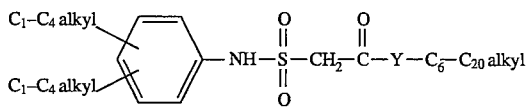

where Y is O, S, or NH, and especially S.

Also preferred are compounds of the formula

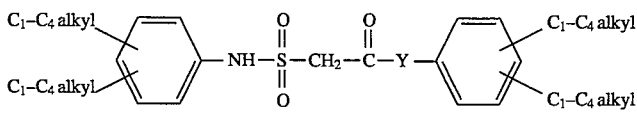

where Y is O, S, or NH, and especially S.

Another class of compounds provided by the invention have the formula

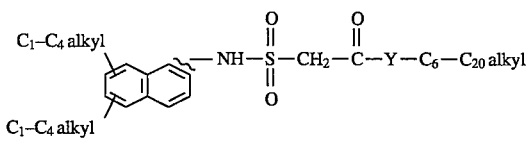

Another class of invention compounds have the formula

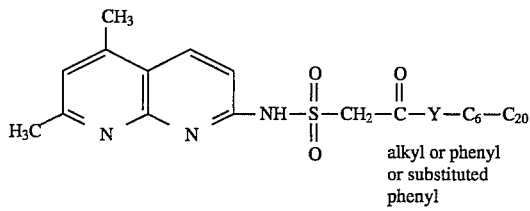

where Y is O, S, or NH, and substituted phenyl is phenyl having 1, 2, or 3 substituents as defined above.

Another preferred group of compounds of the invention have the formula

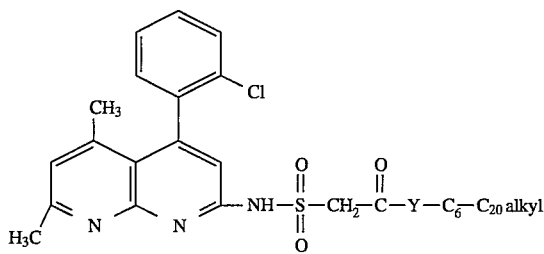

Still other compounds of the invention have the formula

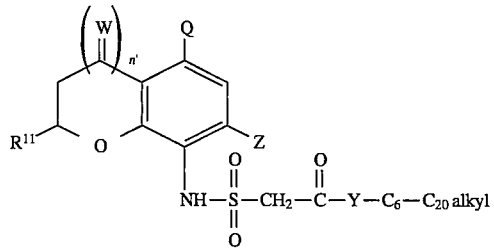

wherein $R_2$, $R_3$, $R_4$, $R_{11}$, W, n', Q, and Z are as defined above, and Y is O, S, or NH.

The compounds of this invention are prepared by any of several synthetic routes utilizing routine methodology well known to those skilled in the art of organic chemistry. The compounds are prepared from readily available starting materials and reactants.

In a preferred embodiment, compounds of Formula II

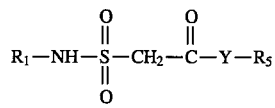

are prepared by reacting an alcohol, thiol, or amine of the formula H—Y—$R_5$ with an aminosulfonyl acetyl halide of the formula

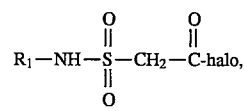

where $R_1$ is as defined above and halo is preferably bromo or chloro. The aminosulfonylacetyl halides are readily prepared by starting with sulfoacetic acid, which can be reacted with an alcohol to give the corresponding sulfoacetic acid ester, which reacts with a halogenating agent to give the corresponding sulfonyl halide. The sulfonyl halide is reacted with an amine $R_1$ $NH_2$ (or $R_1R_2NH$ for compounds wherein $R_2$ is other than hydrogen) to provide the corresponding aminosulfonylacetic acid ester. The ester is readily hydrolyzed to the acid, which is then converted to the corresponding aminosulfonylacetyl halide. The above reaction is depicted by the general scheme of Chart I as follows:

CHART I

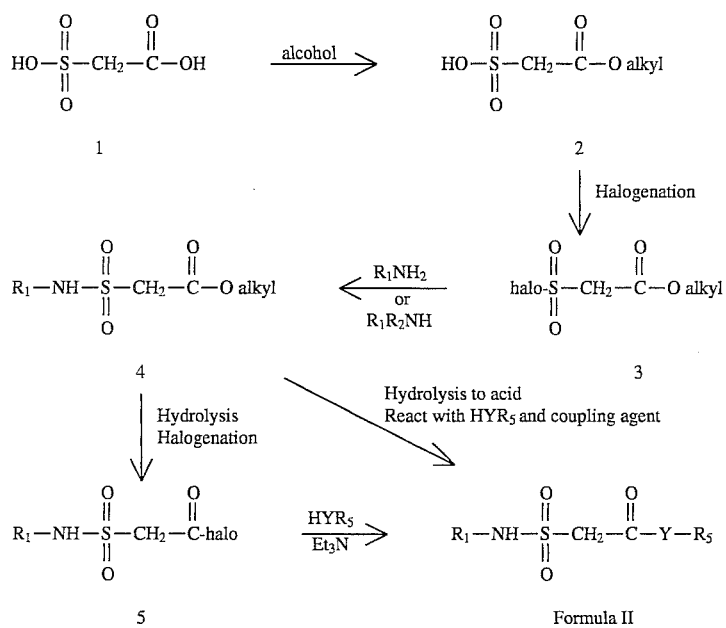

In a typical synthesis, for example, sulfoacetic acid (1) is reacted with ethanol at about 50° C. for 2 hours to give the acetic acid ethyl ester (2 where alkyl is ethyl). The ethyl ester is reacted with a halogenating agent such as phosphorus oxychloride to give the corresponding sulfonylchloride (3 where halo is chloro).

The sulfonyl chloride 3 is reacted with an amine (preferably $R_1NH_2$, although amines $R_1R_2NH$ can be utilized to give N,N-disubstituted sulfonamides) to produce the sulfonamide acetic acid ester 4. The ester 4 is readily converted to an acid halide by first hydrolyzing the ester, for instance by reaction with an alkaline base such as sodium hydroxide or potassium hydroxide to give the sulfonamide acetic acid, and then reacting the acid with a halogenating agent such as oxalyl chloride or the like to give an acid chloride 5. The acid chloride 5 is reacted with about an equimolar quantity of an alcohol, thiol, or amine of the formula $HYR_5$ to give the invention compound of Formula II. This latter reaction typically is carried out in an unreactive organic solvent such as methylene chloride or toluene, and normally is complete in about 2 to 24 hours when carried out at about 20°–60° C. The product of Formula II is readily isolated by routine methods, and purified if desired by crystallization or chromatography over solid supports such as silica, eluting with common solvents such as ethyl acetate, acetone, and the like.

An alternative method for preparing compounds of the invention comprises reacting a sulfonamide acetic acid with an amine, alcohol, or thiol in the presence of a coupling reagent such as those commonly utilized in peptide synthesis. Typical peptide coupling reagents include N,N-dicyclohexylcarbodiimide (DCC), N-ethoxycarbonyl-2-ethoxy-1,2-dihydro-quinoline (EEDQ) and carbonyldiimidazole (CDI). This direct coupling reaction is preferred for preparing invention compounds in which one or both of $R_3$ and $R_4$ of Formula I are other than hydrogen. For example, a preferred class of invention compounds have the formula

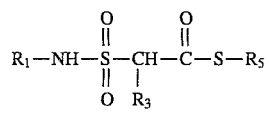

wherein $R_3$ is phenyl or naphthyl, or substituted phenyl or substituted naphthyl as defined above.

The use of a coupling reagent is depicted in Chart I, and is given in more detail in Chart II below:

CHART II

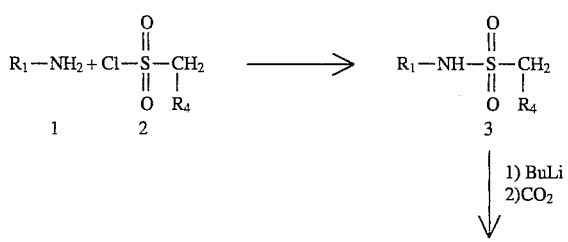

CHART II -continued

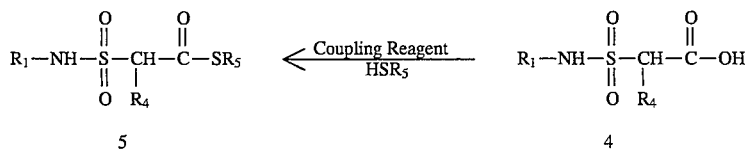

In the above Scheme II, a sulfonyl halide, such as the chloride (2), is reacted with an amine $R_1NH_2$ to give the sulfonamide 3. The sulfonamide is reacted with a strong base such as n-butyl lithium, generally in a solvent such as tetrahydrofuran at a reduced temperature of about −70° C., to produce a lithio salt, which generally is not isolated but is reacted directly with carbon dioxide to give the acetic acid (4). The acetic acid is reacted with an amine $H_2NR_5$, an alcohol $HOR_5$, or as shown in the chart a thiol $HSR_5$, in the presence of a coupling reagent to afford the invention compound (5). The coupling reaction generally is conducted in an unreactive organic solvent such as dichloromethane and normally is complete in about 2 to 24 hours when carried out at about 20° C. to about 60° C. The product (5) is readily isolated by routine procedures such as filtration and evaporation of solvents, and it is further purified if desired by crystallization, chromatography, or the like.

Compounds of Formula I wherein one or both of $R_3$ and $R_4$ are other than hydrogen can alternatively be prepared simply by reacting a Formula I compound in which one or both of $R_3$ and $R_4$ are hydrogen with a strong base such as sodium hydride to form an anion, followed by reaction with a compound of the formula $R_3L$ or $R_4L$, where L is a leaving group such as halogen, especially chloro, iodo, or bromo. This reaction scheme is depicted in Chart III as follows:

CHART III

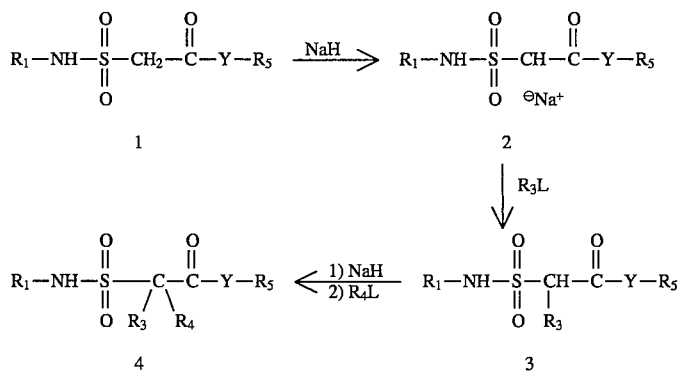

The invention compound (1) is reacted with about 1M equivalent of sodium hydride to give anion (2), which is not isolated but rather is reacted directly with $R_3L$, for example methyl chloride, 1-naphthyl chloride, cyclopropyl iodide, phenyl iodide, or the like, to give the α-substituted sulfonamide acetic acid derivative (3). If desired, the compound (3) can be further reacted with a molar equivalent of sodium hydride, followed by reaction with $R_4L$, to give the α,α-disubstituted compound (4).

The synthesis of specific compounds provided by this invention is presented in the following detailed examples. The examples are illustrative only, and the invention is not limited to the compounds actually made or the synthetic routes utilized.

EXAMPLE 1

2,4,6-Triisopropylphenyl(2,6-diisopropylphenylsulfamoyl)acetate

Sulfoacetic acid (52 g, 371 mM) and EtOH (500 mL) were heated under reflux for 20 hours. The reaction mixture was cooled, and the excess ethanol was removed under vacuum to give ethyl sulfoacetate.

$^1$H NMR ($CDCl_3$):δ1.35 (t, 3H), 4.1 (s, 2H), 4.25 (q, 2H). A mixture of ethyl sulfoacetate (16.82 g, 100 mM) and $POCl_3$ (30.67 g, 200 mM) was heated at 125° C. for 5 hours. The mixture was cooled and filtered, and excess $POCl_3$ was removed to give ethyl chlorosulfonylacetate. The ethyl chlorosulfonylacetate (8.18 g, 43.83 mM) was added dropwise with stirring to a solution of 2,6-diisopropylaniline (15.54 g, 87.66 mM) in 50 mL $CH_2Cl_2$ maintained at 0° C. The mixture was stirred at room temperature for an additional 18 hours. The solvent was removed and the residue was redissolved in 100 mL ethyl acetate and washed with 1N HCl and brine. The ethyl acetate was evaporated and the pure compound was isolated by chromatography over silica gel (EtOAc/hexane, 1:4 as eluant) as a white powder identified as ethyl (2,6-diisopropylphenylsulfamoyl)acetate, 7.0 g (≈50%), mp 74°–77° C.

Ethyl (2,6-diisopropylphenylsulfamoyl) acetate (4.9 g, 15 mM) and KOH (2.1 g, 37.5 mM) were mixed in 15 mL $H_2O$ and 6 mL EtOH. The mixture was heated under reflux for 2.5 hours, charcoal was added, and heating was continued for another 10 minutes. The mixture was filtered and the extracted with ether, the aqueous layer was acidified with concentrated HCl, and extracts were combined and evaporated to yield a total weight of 1.49 g (33%) of (2,6-diisopropylphenylsulfamoyl)acetic acid.

(2,6-Diisopropylphenylsulfamoyl)acetic acid (1.0 g, 3.3 mM) and 2,4,6-triisopropylphenol (0.74 g, 3.3 mL) were mixed in 100 mL of dichloromethane at 0° C. under an atmosphere of $N_2$. A catalytic amount (5 mg) of 4-dimethylaminopyridine was added followed by 0.69 g (3.3 mM) of N,N'-dicyclohexylcarbodiimide. The resulting mixture was gradually warmed to room temperature and then heated to reflux for 4 hours. The mixture was cooled to room temperature and stirred for an additional 16 hours. The reaction mixture was filtered to remove the solids. The filtrate was concentrated and chromatographed on silica gel using 10% ethyl acetate in hexanes to give 0.26 g of 2,4,6-triisopropylphenyl(2,6-diisopropylphenylsulfamoyl)acetate as a white solid, mp 128°–130° C.

$^1$H NMR (CDCl$_3$):δ1.03–1.37 (m, 30H), 2.83–3.0 (m, 1H), 3.1–3.28 (m, 2H), 3.3–3.6 (m, 2H), 4.3 (s, 2H), 7.03–7.4 (m, 5H), 8.1 (b, 1H, NH).

EXAMPLE 2

2-(2,6-Diisopropyl-phenylsulfamoyl)-N-(dodecyl-2-H-tetrazol-5-yl)-acetamide

Oxalylchloride (2 mL, 23 mM) DMS (1 drop) were added to a solution of (2,6-diisopropylphenylsulfamoyl) acidic acid (2 g, 6.68 mM) and 20 mL toluene. The solution was stirred at room temperature for 12 hours. the excess oxalylchloride and toluene were removed by evaporation under reduced pressure and the residue was dissolved in 30 mL THF. This solution was added slowly to a solution of 2-dodecyl-5-amino-tetrazole (2-DAT) (1.7 g, 6.68 mM) and 10 mL of THF. The mixture was stirred at room temperature for 12 hours, and then thin layer chromatography on silica plates showed disappearance of starting material. The solvent was evaporated and the solid was redissolved in EtOAc (20 mL), washed with brine and dried over MgSO$_4$. The solvent was removed by evaporation under reduced pressure to give a solid. The product was purified by column chromatography over silica gel (hexane/EtOAc= 1/1), to provide, following evaporation of the solvent from the appropriate fraction, a white product; weight 1.5 g (42%), mp 138°–140° C.

$^1$H MNR (CDCL$_3$):λ0.9 (t, 3H), 1.15–1.4 (m, 30H), 1.91–2.08 (m, 2H), 3.4–3.6 (m, 2H), 4.4 (s, 1H, NH), 4.58 (t, 2H), 7.18–7.5 (m, 3H, Ar).

EXAMPLE 3

2-(2,6-Diisopropylphenylsulfamoyl)-N,N-dioctylacetamide

This compound was prepared in the same manner as for the title compound of Example 2, except that 2-DAT was replaced with N,N-dioctylamine, mp 107°–109° C.

EXAMPLE 4

N-(2,6-Diisopropylphenyl)-2-(2,6-diisopropylphenylsulfamoyl)-acetamide

This compound was prepared in the same manner as for the title compound of Example 2, except that 2-DAT was replaced with 2,6-diisopropylaniline, mp 202°–205° C.

EXAMPLE 5

2-(2,6-Diisopropylphenylsulfamoyl)-N-dodecyl-acetamide

This compound was prepared in the same manner as for the title compound of Example 2, except that 2-DAT was replaced with N-dodecylamine, mp 83°–85° C.

EXAMPLE 6

2-(2,6-Diisopropylphenylsulfamoyl)-N-hexyl-acetamide

This compound was prepared in the same manner as for the title compound of Example 2, except that 2-DAT was replaced with N-hexylamine, mp 125°–127° C.

EXAMPLE 7

N-Benzyl-N-isopropyl-2-(2,6-diisopropylphenylsulfamoyl)acetamide

This compound was prepared in the same manner as for the title compound of Example 2, except that 2-DAT was replaced with N-isopropyl-N-benzylamine, mp 168°–170° C.

EXAMPLE 8

2-(2,6-Diisopropylphenylsulfamoyl)-N-diphenylmethylacetamide

This compound was prepared in the same manner as for the title compound of Example 2, except that 2-DAT was replaced with diphenylmethylamine, mp 166°–167° C.

EXAMPLE 9

2-(2,6-Diisopropylphenylsulfamoyl)-N-(2-cyclopentyl-2-phenylethyl)-acetamide

This compound was prepared in the same manner as for the title compound of Example 2, except that 2-DAT was replaced with 2-cyclopentyl-2-phenylethylamine, mp 168°–170° C.

EXAMPLE 10

(2,6-Diisopropylphenylsulfamoyl)-thio-acetic Acid S-dodecyl Ester

This compound was prepared in the same manner as for the title compound of Example 2, except that 2-DAT was replaced with dodecylthiol, mp 58°–60° C.

EXAMPLE 11

(2,6-Diisopropylphenylsulfamoyl)-thio-acetic Acid S-octyl Ester

This compound was prepared in the same manner as for the title compound of Example 2, except that 2-DAT was replaced with octanthiol, mp 51°–52° C.

EXAMPLE 12

(2,6-Diisopropylphenylsulfamoyl)-thioacetic Acid 2,6-Diisopropylphenyl Ester

This compound was prepared in the same manner as for the title compound of Example 2, except that 2-DAT was replaced with 2,6-diisopropylthiophenol, mp 169°–171° C.

EXAMPLE 13

(2,6-Diisopropylphenylsulfamoyl)-thioacetic Acid S-hexyl Ester

This compound was prepared in the same manner as for the title compound of Example 2, except that 2-DAT was replaced with hexanthiol, mp 81°–83° C.

EXAMPLE 14

(2,6-Diisopropylphenylsulfamoyl)-thioacetic Acid S-decyl Ester

This compound was prepared in the same manner as for the title compound of Example 2, except that 2-DAT was replaced with decanthiol, mp 57°–59° C.

EXAMPLE 15

(2,6-Diisopropylphenylsulfamoyl)-thio-acetic Acid S-tetradecyl Ester

This compound was prepared in the same manner as for the title compound of Example 2, except that 2-DAT was replaced with tetradecanethiol.

$^1$H NMR (CDCl$_3$):δ7.15–7.35 (m, 3H); 6.4 (s, 1H); 4.35 (s, 2H); 3.38–3.5 (m, 2H); 3.05 (t, 2H); 1.15–1.4 (m, 24H); 0.89 (t, 3H).

EXAMPLE 16

(2,4-Diifluorophenylsulfamoyl)-thioacetic Acid S-dodecyl Ester

This compound was prepared in the same manner as for the title compound of Example 2, except that 2,6-diisopropylaniline was replaced with 2,4-difluoroaniline and 2-DAT was replaced with dodecanthiol.

$^1$H NMR (CDCl$_3$):δ7.5–7.65 (m, 1H); 7.05 (S, NH); 6.85–7.0 (m, 2H); 4.15 (s, 2H); 2.95 (t, 2H); 1.5–1.68 (m, 2H); 1.2–1.4 (m, 18H); 0.88 (t, 3H).

EXAMPLE 17

(2,4,6-Trimethoxyphenylsulfamoyl)-thioacetic Acid S-dodecyl Ester

This compound was prepared in the same manner as for the title compound of Example 2, except that 2,6-diisopropylaniline was replaced with 2,4,6-triisopropoxylaniline and 2-DAT was replaced with dodecanthiol, mp 90°–93° C.

EXAMPLE 18

(2,6-Diisopropylphenylsulfamoyl)-thioacetic Acid S-octadecyl Ester

This compound was prepared in the same manner as for the title compound of Example 2, except that 2-DAT was replaced with octadecanthiol.

$^1$H NMR (CDCl$_3$):δ7.15–7.35 (m, 3H) 6.3 (s, 1H); 4.35 (s, 2H); 3.35–3.5 (m, 2H); 3.02 (t, 2H); 1.58–1.7 (m, 2H); 1.2–1.5 (m, 30H); 0.88 (m,3H).

EXAMPLE 19

(2,6-Diisopropylphenylsulfamoyl)-thioacetic Acid S-2,6-dimethylphenyl Ester

This compound was prepared in the same manner as for the title compound of Example 2, except that 2-DAT was replaced with 2,6-dimethylthiophenol, mp 149–152.

EXAMPLE 20

(2,6-Diisopropylphenylsulfamoyl)-acetic Acid Tetradecyl Ester

This compound was prepared in the same manner as for the title compound of Example 2, except that 2-DAT was replaced with tetradecanol, mp 53°–55° C.

EXAMPLE 21

(2,6-Diisopropylphenylsulfamoyl)-acetic Acid Ethyl Ester

This compound was described in the experimental section of Example 1, mp 74°–77° C.

EXAMPLE 22

2,6,-Diissoproplphenyl(2,6-diisopropylphenylsulfamoyl)acetate

This compound was prepared in the same manner as for the title compound of Example 1, except that 2,4,6-triisopropylphenol was replaced with 2,6-diisopropylphenol, mp 178°–180° C.

EXAMPLE 23

(2,6-Diisopropylphenylsulfamoyl)-acetic Acid Octyl Ester

This compound was prepared in the same manner as for the title compound of Example 2, except that 2-DAT was replaced with octanol, mp 56°–58° C.

EXAMPLE 24

(2,6-Diisopropylphenylsulfamoyl)-acetic Acid Decylester

This compound was prepared in the same manner as for the title compound of Example 2, except that 2-DAT was replaced with decanol, mp 65°–67° C.

EXAMPLE 25

(2,6-Diisopropylphenylsulfamoyl)-acetic Acid 2,4,6-trimethoxyphenyl Ester

This compound was prepared in the same manner as for the title compound of Example 1, except that 2,4,6-triisopropylphenol was replaced with 2,4,6-trimethoxyphenol, mp 167°–170° C.

EXAMPLE 26

(2,6-Diisopropylphenylsulfamoyl)-acetic Acid Hexyl Ester

This compound was prepared in the same manner as for the title compound of Example 2, except that 2-DAT was replaced with hexanol, mp 66°–68° C.

EXAMPLE 27

N-(2,4,6-trimethyoxyphenyl)-2-(2,4,6-trimethoxyphenylsulfamoyl)-acetamide

This compound was prepared in the same manner as for the title compound of Example 2, except that 2,6-diisopropylaniline and 2-DAT were replaced with 2,4,6-trimethoxyaniline, mp 180°–182° C.

EXAMPLE 28

(2,6-Diisopropylphenylsulfamoyl)-acetic Acid 1-methyltridecyl Ester

This compound was prepared in the same manner as for the title compound of Example 2, except that 2-DAT was replaced with 1-methyl-tridecanol.

$^1$H NMR (CDCl$_3$):δ7.15–7.35 (m, 3H); 6.4 (s, 1H); 5.05–5.15 (m, 1H); 4.15 (s, 2H); 3.35–3.55 (m, 2H); 1.15–1.45 (m, 25H); 0.89 (t, 3H).

EXAMPLE 29

(2,6-Diisopropylphenylsulfamoyl)-acetic Acid Dodecylester

This compound was prepared in the same manner as for the title compound of Example 2, except that 2-DAT was replaced with dodecanol, mp 58°–59° C.

EXAMPLE 30

(2,6-Diisopropylphenylsulfamoyl)-acetic Acid

This compound was described in experimental section of Compound 1, mp 153°–155° C.

EXAMPLE 31

(2,4,6-Triisopropylphenylsulfamoyl)-acetic Acid, 2,6-Diisopropyl Ester

This compound was prepared in the same manner as for the title compound of Example 1, except that 2,6-diisopropylaniline was replaced with 2,4,6-triisopropylaniline and 2,4,6-triisopropylphenol was replaced with 2,6-diisopropylphenol, mp 165°–167° C.

EXAMPLES 32–58

By following the general procedures of Example 1 or 2, the following compounds can be prepared:

32. (N,N-dioctylsulfamoyl)-acetic acid, 2,6-diisopropylphenyl ester
33. (N,N-di-sec-butylsulfamoyl)-acetic acid, 2,6-diisopropylphenyl ester
34. (2,4,6-tri-t-butylphenylsulfamoyl)-acetic acid, 2,6-diisopropylphenyl ester
35. (3-methyl-2-pyridylsulfamoyl)-acetic acid, 2,6-diisopropylphenyl ester
36. (2,4,6-tri-t-butylphenylsulfamoyl)-acetic acid, n-dodecyl ester
37. (2,4,6-tri-t-butylphenylsulfamoyl)-acetic acid, 2-tetradecyl ester
38. (3-methyl-2-pyridylsulfamoyl)-acetic acid, n-dodecyl ester
39. (3-methyl-2-pyridylsulfamoyl)-acetic acid, 2-tetradecyl ester
40. (2,6-diisopropylphenylsulfamoyl)-acetic acid, (2-methyl-4-phenylbutyl) ester
41. (2,4,6-tri-t-butylphenylsulfamoyl)-acetic acid, (2-methyl-4-phenylbutyl) ester
42. (3-methyl-2-pyridylsulfamoyl)-acetic acid, (2-methyl-4-phenylbutyl) ester
43. 2-(N,N-dioctylsulfamoyl)-N-(2,6-diisopropylphenyl)acetamide
44. 2-(N,N-di-sec-butylsulfamoyl)-N-(2,6-diisopropylphenyl)acetamide
45. 2-(n-Dodecylsulfamoyl)-N-(2,6-diisopropylphenyl)acetamide
46. (n-Dodecylsulfamoyl)-acetic acid, 2,6-diisopropylphenyl ester
47. 2-(N,N-dioctylsulfamoyl)-N-(2,4,6-tri-t-butylphenyl)acetamide
48. 2-(N,N-di-sec-butylsulfamoyl)-N-(2,4,6-tri-t-butylphenyl)acetamide
49. 2-(n-Dodecylsulfamoyl)-N-(2,4,6-tri-t-butylphenyl)acetamide
50. 2-(n-Dodecylsulfamoyl)-N-(3-methyl-2-pyridyl)acetamide
51. 2-(N,N-Dioctylsulfamoyl)-N-(3-methyl-2-pyridyl)acetamide
52. 2-(N,N-Di-sec-butylsulfamoyl)-N-(3-methyl- 2-pyridyl)acetamide
53. (2,6-Diisopropylphenylsulfamoyl)-phenylacetic acid, 2,6-diisopropylphenyl ester
54. (2,6-Diisopropylphenylsulfamoyl)-phenylacetic acid, n-dodecyl ester
55. (2,4,6-Triisopropylphenylsulfamoyl)-phenylacetic acid, 2,6-diisopropylphenyl ester
56. (2,4,6-Triisopropylphenylsulfamoyl)-phenylacetic acid, n-dodecyl ester
57. (2,6-Diisopropylphenylsulfamoyl)-phenyl thioacetic acid, S-n-dodecyl ester
58. (2,6-Diisopropylphenylsulfamoyl)-thioacetic acid, S-2-tetradecyl ester The compounds of the present invention are potent inhibitors of the enzyme acyl-CoA: cholesterol acyltransferase (ACAT), and are thus effective in inhibiting the esterification and transport of cholesterol across the intestinal cell wall. The compounds of the present invention are thus useful in pharmaceutical formulations for the treatment of hypercholesterolemia and atherosclerosis, and in general lipid regulation.

The ability of representative compounds of the present invention to inhibit ACAT was measured using an in vitro test more fully described in F. J. Field and R. G. Salone, *Biochemica et Biophysica Acta*, 712:557–570 (1982). The test assesses the ability of a test compound to inhibit the acylation of cholesterol by oleic acid by measuring the amount of radiolabeled cholesterol oleate formed from radiolabeled oleic acid in a tissue preparation containing rat liver microsomes (designated LAI).

These data appear in Table 1 where they are expressed as IC$_{50}$ values; i.e., the micromolar concentration of test compound required to inhibit the activity of the enzyme by 50%.

In an in vivo screen designated APCC, male Sprague-Dawley rats (200–225 g body weight) were randomly divided into treatment groups and dosed at 4 PM with either vehicle (CMC/Tween) or suspensions of invention compounds in vehicle. The normal chow diet was then replaced with a high fat, high cholesterol diet (5.5% peanut oil, 1.5% cholesterol, and 0.5% cholic acid). The rats consumed this diet ad libitum during the night and were sacrificed at 8 AM to obtain blood samples for cholesterol analysis using standard procedures. Statistical differences between mean cholesterol values for the same vehicle were determined using analysis of variance followed by Fisher's least significant test. The results of this trial for representative compounds of the present invention also appear in Table I as the percent change in total cholesterol (% TC) from control animals given vehicle and diet only. All compounds in the APCC test reported in Table 1 were administered by gavage at 30 mg/kg.

TABLE 1

| Compound of Example | LAI ($IC_{50}$, µM) | APCC (% change TC) |
|---|---|---|
| 1 | 2.8 | −19 |
| 2 | 1.9 | −50 |
| 3 | 4.2 | −19 |
| 4 | 0.351 | −51 |
| 5 | 0.32 | −29 |
| 6 | >5.0 | −16 |
| 7 | 0.15 | −31 |
| 8 | >1.0 | |
| 9 | >1.0 | |
| 10 | 0.073 | −71 |
| 11 | 0.15 | −32 |
| 12 | >5.0 | −16 |
| 13 | 1.0 | |
| 14 | 0.13 | |
| 15 | 0.036 | −23 |
| 16 | 0.23 | −37 |
| 17 | 0.57 | −3 |
| 18 | >5.0 | −35 |
| 19 | >5.0 | +3 |
| 20 | 0.23 | −45 |
| 21 | >1.0 | +2 |
| 22 | 17.6 | −7 |
| 23 | >1.0 | −4 |
| 24 | >1.0 | −16 |
| 25 | >1.0 | −6 |
| 26 | >1.0 | −5 |
| 27 | 7.6 | +5 |
| 28 | 0.021 | −39 |
| 29 | 0.11 | −34 |
| 30 | >1.0 | +3 |
| 31 | >1.0 | −29 |
| 40 | 4.2 | −32 |

In therapeutic use as agents for treating hypercholesterolemia or atherosclerosis, the compounds of Formula I or pharmaceutically acceptable salts thereof are administered to the patient at a dosage which is effective in inhibiting ACAT. Such ACAT-inhibiting levels generally are from about 50 to about 3000 mg per day, ideally from about 100 to about 1000 mg per day. For a normal human adult of approximately 70 kg of body weight, a typical dosage of from about 1 to about 40 mg/kg of body weight per day will be utilized. The specific dosages employed, however, may be varied depending upon the requirements of the patient, the severity of the condition being treated, and the activity of the compound being employed. The determination of optimum dosages for a particular situation is within the skill of the art.

For preparing the pharmaceutical compositions from the compounds of this invention, inert, pharmaceutically acceptable carriers can be either solid or liquid. Solid form preparations include powders, tablets, dispersible granules, capsules, and cachets.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

Powders and tablets preferably contain between about 5% to about 70% by weight of the active ingredient. Suitable carriers are magnesium dicarbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without carriers) is surrounded by a carrier, which is thus in association with it. In a similar manner, cachets are also included.

Tablets, powders, cachets, and capsules can be used as solid dosage forms suitable for oral administration. Sustained-release formulation can be prepared utilizing conventional techniques such as polymers, osmotic pumps, wax, and the like.

Liquid form preparations include solutions, suspensions, or emulsions suitable for oral administration. Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethylcellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation containing discrete quantities of the preparation, for example, packeted tablets, capsules, and powders in vials or ampoules. The unit dosage form can also be a capsule, cachet, or tablet itself, or it can be the appropriate number of these packaged forms.

The following examples further illustrate typical pharmaceutical formulations provided by this invention.

EXAMPLE 59

A pharmaceutical formulation in the form of hard gelatin capsules for oral administration are prepared using the following ingredients:

| | Quantity (mg/capsule) |
|---|---|
| Active compound | 250 |
| Starch powder | 200 |
| Magnesium stearate | 10 |
| Total | 460 mg |

The above ingredients are mixed and filled into hard gelatin capsules in 460 mg quantities. A typical active ingredient is (2,6-diisopropylphenylsulfamoyl)thioacetic acid 1,1-dimethylheptyl ester.

EXAMPLE 60

| Formulation for Oral Suspension | |
| --- | --- |
| Ingredient | Amount |
| 2-(2,6-di-tert-butylphenylsulfamoyl)-N-(2-isohexyl-2H-tetrazol-5-yl)acetamide | 500 mg |
| Sorbitol solution (70% N.F.) | 40 mL |
| Sodium benzoate | 150 mg |
| Saccharin | 10 mg |
| Cherry flavor | 50 mg |
| Distilled water q.s. ad | 100 mL |

The sorbitol solution is added to 40 mL of distilled water and the tetrazole acetamide is suspended therein. The saccharin, sodium benzoate, and flavoring are added and dissolved. The volume is adjusted to 100 mL with distilled water. Each milliliter of syrup contains 5 mg of active ingredient.

EXAMPLE 61

Tablets each containing 60 mg of active ingredient.

| | |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1.0 mg |
| Total | 150 mg |

The active ingredients, starch and cellulose, are passed through a No. 45 mesh U.S. sieve and mixed thoroughly. The solution of polyvinylpyrrolidone is mixed with the resultant powders and then passed through a No. 14 mesh U.S. sieve. The granules are dried at 50°–60° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

A typical active ingredient utilized in the above preparation is the compound of Example 16.

EXAMPLE 62

A parenteral composition suitable for administration by injection is prepared by dissolving 100 mg of 2-(6-methyl-1-naphthylsulfamoyl)-N-(5-cyclobutyl- 6-phenylheptyl)acetamide in 250 mL of 0.9% aqueous sodium chloride solution and adjusting the pH of the solution to about 7.0.

EXAMPLE 63

Preparation for Suppositories

A mixture of 500 mg of 2-(n-dodecylsulfamoyl)-N-(2,4,6-trichlorphenyl)acetamide and 1500 mg of theobroma oil are blended to uniformity at 60° C. The mixture is cooled to 24° C. in tapered molds. Each suppository will weight about 2 g and can be administered from 1 to 2 times each day for regulation of lipids and treatment of hypercholesterolemia.

What is claimed is:

1. A compound of Formula I

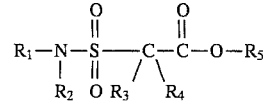

wherein $R_1$ is selected from
(a) phenyl which is unsubstituted or is substituted with from 1 to 3 substituents selected from $C_1$–$C_4$ alkyl, $C_1$–$C_4$ alkoxy, $C_1$–$C_4$ alkylthio, hydroxy, halo, nitro, cyano, trifluoromethyl,

—COOH,

—COOalkyl wherein alkyl has from 1 to 4 carbon atoms and which is straight or branched, —$(CH_2)_m NR_x R_y$ wherein m is 0 or 1, and each of $R_x$ and $R_y$ is independently hydrogen or $C_1$–$C_4$ alkyl;

(b) 1- or 2-naphthyl which is unsubstituted or substituted with from 1 to 3 substituents selected from $C_1$–$C_4$ alkyl, $C_1$–$C_4$ alkoxy, $C_1$–$C_4$ alkylthio, hydroxy, halo, nitro, cyano, trifluoromethyl,

—COOH,

—COOalkyl wherein alkyl has from 1 to 4 carbon atoms and which is straight or branched, —$(CH_2)_m NR_x R_y$ wherein m is 0 or 1, and each of $R_x$ and $R_y$ is independently hydrogen or $C_1$–$C_4$ alkyl;

(c) a straight or branched hydrocarbon group having from 1 to 18 carbon atoms which is saturated or is unsaturated containing one double bond or two nonadjacent double bonds; or (d) a cycloalkyl group having from 3 to 10 carbon atoms; $R_2$ is hydrogen or a group defined as for $R_1$;

$R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, 1- or 2-naphthyl, or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl; or $R_3$ and $R_4$ taken together with the carbon to which they are attached complete a $C_3$–$C_8$ carbocyclic ring;

$R_5$ is $R_6$, $C_8$–$C_{20}$ alkyl, $C_2$–$C_{20}$ alkenyl, $C_2$–$C_{20}$ alkynyl and alkyl, alkenyl and alkenyl substituted with one or two groups defined by $R_6$, where $R_6$ is $C_3$–$C_6$ cycloalkyl, phenyl, 1- or 2-naphthyl, and phenol and naphthyl substituted with from 1 to 3 substituents selected from:

$C_1$–$C_4$ alkyl, $C_1$–$C_4$ alkoxy, $C_1$–$C_4$ alkylthio, phenyl,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is hydrogen or a straight chain alkyl group having 1 to 4 carbon atoms; and $R_6$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with amino, halo, nitro, hydroxy, cyano, trifluoromethyl, or an alkyl group having from 1 to 20 carbon atoms and the N-oxides thereof.

2. A compound of claim 1 wherein $R_1$ is phenyl or phenyl substituted with 1, 2, or 3 substituents selected from $C_1$–$C_4$ alkyl and $C_1$–$C_4$ alkoxy.

3. A compound of claim 2 wherein $R_5$ is phenyl or phenyl substituted with 1, 2, or 3 substituents selected from $C_1$–$C_4$ alkyl or $C_1$–$C_4$ alkoxy.

4. The compound of claim 4 which is 2,4,6-triisopropylphenyl-( 2,6-diisopropylphenylsulfamoyl)acetate;
2,6,-diisoproplphenyl(2,6-diisopropylphenylsulfamoyl)acetate;
(2,6-diisopropylphenylsulfamoyl)-acetic acid 2,4,6-trimethoxyphenyl ester; and
(2,4,6-triisopropylphenylsulfamoyl)-acetic acid, 2,6-diisopropyl ester.

5. A compound of claim 2 wherein $R_5$ is $C_8$–$C_{20}$ alkyl

6. The compound of claim 5 which is (2,6-diisopropylphenylsulfamoyl)-acetic acid tetradecylester;
(2,6-diisopropylphenylsulfamoyl)-acetic acid octylester;
(2,6-diisopropylphenylsulfamoyl)-acetic acid decylester;
(2,6-diisopropylphenylsulfamoyl)-acetic acid hexylester;
(2,6-diisopropylphenylsulfamoyl)-acetic acid 1-methyltridecyl ester; and
(2,6-diisopropylphenylsulfamoyl)-acetic acid dodecyl ester.

7. A compound of Formula II

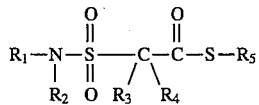

wherein $R_1$ is selected from
(a) phenyl which is unsubstituted or is substituted with from 1 to 3 substituents selected from $C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is independently hydrogen or $C_1$–$C_4$ alkyl;

(b) 1- or 2-naphthyl which is unsubstituted or substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is independently hydrogen or $C_1$–$C_4$ alkyl;

(c) a straight or branched hydrocarbon group having from 1 to 18 carbon atoms which is saturated or is unsaturated containing one double bond or two nonadjacent double bonds; or
(d) a cycloalkyl group having from 3 to 10 carbon atoms;

$R_2$ is hydrogen or a group defined as for $R_1$;

$R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, phenyl, 1- or 2-naphthyl, or phenyl or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl; or $R_3$ and $R_4$ taken together with the carbon to which they are attached complete a $C_3$–$C_8$ carbocyclic ring;

$R_5$ is $R_6$, $C_1$–$C_{20}$ alkyl, $C_2$–$C_{20}$ alkenyl, $C_2$–$C_{20}$ alkynyl and alkyl, alkenyl and alkenyl substituted with one or two groups defined by $R_6$, where $R_6$ is hydrogen, $C_3$–$C_6$ cycloalkyl, phenyl, 1- or 2-naphthyl, and phenyl and naphthyl substituted with from 1 to 3 substituents selected from:
$C_1$–$C_4$ alkyl,
$C_1$–$C_4$ alkoxy,
$C_1$–$C_4$ alkylthio,
phenyl,
hydroxy,
halo,
nitro,
cyano,
trifluoromethyl,
—COOalkyl wherein alkyl has from 1 to 4 carbon atoms and which is straight or branched,
—$(CH_2)_m NR_x R_y$ wherein m is 0 or 1, and each of $R_x$ and $R_y$ is hydrogen or a straight chain alkyl group having 1 to 4 carbon atoms; and $R_6$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with amino, halo, nitro, hydroxy, cyano, trifluoromethyl, or an alkyl group having from 1 to 20 carbon atoms and the N-oxides thereof.

8. A compound of claim 7 wherein $R_5$ is phenyl or phenyl substituted with 1, 2, or 3 groups selected from $C_1$–$C_4$ alkyl and $C_1$–$C_4$ alkoxy.

9. The compound of claim 8 which is (2,6-diisopropylphenylsulfamoyl)-thioacetic acid 2,6-diisopropylphenyl ester; and 2,6-diisopropylphenylsulfamoyl)-thioacetic acid S-2,6-dimethylphenyl ester.

10. A compound of claim 7 wherein $R_5$ is $C_8$–$C_{20}$ alkyl.

11. The compound of claim 10 which is (2,6-diisopropylphenylsulfamoyl)-thioacetic acid S-dodecylester;
(2,6-diisopropylphenylsulfamoyl)-thioacetic acid S-octyl ester;
(2,6-diisopropylphenylsulfamoyl)-thioacetic acid S-hexyl ester;
(2,6-diisopropylphenylsulfamoyl)-thioacetic acid S-decyl ester;
(2,6-diisopropylphenylsulfamoyl)-thioacetic acid S-tetradecyl ester;
(2,4,6-trimethoxyphenylsulfamoyl)-thioacetic acid S-dodecyl ester; and
(2,6-diisopropylphenylsulfamoyl)-thioacetic acid S-octadecyl ester.

12. A compound of claim 8 wherein $R_1$ is phenyl or phenyl substituted with 1, 2, or 3 halo groups.

13. The compound of claim 10 which is (2,4-difluorophenylsulfamoyl)-thioacetic acid S-dodecyl ester.

14. A compound of Formula III

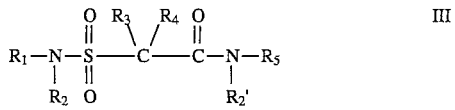

wherein $R_1$ is selected from
(a) phenyl which is unsubstituted or is substituted with from 1 to 3 substituents selected from $C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is independently hydrogen or $C_1$–$C_4$ alkyl;
(b) 1- or 2-naphthyl which is unsubstituted or substituted with from 1 to 3 substituents selected from
$C_1$–$C_4$ alkyl,
$C_1$–$C_4$ alkoxy,
$C_1$–$C_4$ alkylthio,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is independently hydrogen or $C_1$–$C_4$ alkyl;
(c) a straight or branched hydrocarbon group having from 8 to 18 carbon atoms which is saturated or is unsaturated containing one double bond or two nonadjacent double bonds; or
(d) a cycloalkyl group having from 3 to 10 carbon atoms;
$R_2$ is hydrogen or a group defined as for $R_1$;

$R_3$ and $R_4$ independently are $C_3$–$C_6$ cycloalkyl, hydroxy-$C_1$–$C_4$ alkyl, $C_1$–$C_4$ alkoxy, hydrogen, $C_1$–$C_4$ alkyl, 1- or 2-naphthyl, or naphthyl substituted with from 1 to 3 substituents selected from $C_1$–$C_4$ alkyl, $C_1$–$C_4$ alkoxy, $C_1$–$C_4$ alkylthio, halo, nitro, cyano, trifluoromethyl, phenyl, or $C_3$–$C_8$ cycloalkyl; or $R_3$ and $R_4$ taken together with the carbon to which they are attached complete a $C_3$–$C_8$ carbocyclic ring;

$R_2'$ is $R_2$ as defined above;

$R_5$ is $R_6$, $C_1$–$C_{20}$ alkyl, $C_2$–$C_{20}$ alkenyl, $C_2$–$C_{20}$ alkynyl and alkyl, alkenyl and alkenyl substituted with one or two groups defined by $R_6$, where $R_6$ is $C_3$–$C_6$ cycloalkyl, 1- or 2-naphthyl, and phenyl and naphthyl substituted with from 1 to 3 substituents selected from:
$C_1$–$C_4$ alkyl,
$C_1$–$C_4$ alkoxy,
$C_1$–$C_4$ alkylthio,
phenyl,
hydroxy,
halo,
nitro,
cyano,
trifluoromethyl,
—COOH,
—COOalkyl wherein alkyl has from 1 to 4 carbon atoms and which is straight or branched,
—$(CH_2)_m NR_x R_y$ wherein m is 0 or 1, and each of $R_x$ and $R_y$ is hydrogen or a straight chain alkyl group having 1 to 4 carbon atoms; and $R_6$ is heteroaryl selected from a 5- or 6-membered monocyclic or fused bicyclic heterocyclic group containing at least 1 to 4 heteroatoms in at least one ring, said heteroatoms being nitrogen, oxygen, or sulfur and combinations thereof, said heterocyclic group being unsubstituted or substituted with amino, halo, nitro, hydroxy, cyano, trifluoromethyl, or an alkyl group having from 1 to 20 carbon atoms and the N-oxides thereof.

15. A compound of claim 14 wherein $R_2'$ is hydrogen.

16. A compound of claim 15 wherein $R_5$ is phenyl or phenyl substituted with 1, 2, or 3 groups selected from $C_1$–$C_4$ alkyl and $C_1$–$C_4$ alkoxy.

17. The compound of claim 16 which is N-(2,6-diisopropylphenyl)- 2-(2,6-diisopropylphenylsulfamoyl)-acetamide and N-(2,4,6-trimethyoxyphenyl)- 2-(2,4,6-trimethoxy-phenylsulfamoyl)-acetamide.

18. A compound of claim 14 wherein $R_5$ is $C_8$–$C_{20}$ alkyl.

19. The compound of claim 18 which is 2-(2,6-diisopropylphenylsulfamoyl)-N-dodecyl-acetamide and 2-(2,6-diisopropylphenylsulfamoyl)-N-hexyl-acetamide.

20. A compound of claim 14 wherein $R_5$ is tetrazole substituted with $C_8$–$C_{20}$ alkyl.

21. The compound of claim 20 which is 2-(2,6-diisopropylphenylsulfamoyl)-N-( 2-dodecyl-2-H-tetrazol-5-yl)-acetamide.

22. The compound of claim 14 which is 2-(2,6-diisopropylphenylsulfamoyl)-N,N-dioctylacetamide;
N-benzyl-2-(2,6-diisopropylphenylsulfamoyl)-N-isopropylacetamide;
2-(2,6-diisopropylphenylsulfamoyl)-N-diphenylmethyl-acetamide; and
2-(2,6-diisopropylphenylsulfamoyl)-N-(2-cyclopentyl-2-phenylethyl)-acetamide.

23. A pharmaceutical formulation for treating hypercholesterolemia or atherosclerosis comprising an ACAT-inhibiting amount of a compound of claim 1 together with a pharmaceutically acceptable carrier, diluent, or excipient therefor.

24. A pharmaceutical formulation for treating hypercholesterolemia or atherosclerosis comprising an ACAT-inhibiting amount of a compound of claim 7 together with a pharmaceutically acceptable carrier, diluent, or excipient therefor.

25. A pharmaceutical formulation for treating hypercholesterolemia or atherosclerosis comprising an ACAT-inhibiting amount of a compound of claim 14 together with a pharmaceutically acceptable carrier, diluent, or excipient therefor.

26. A formulation of claim 23 employing a compound wherein $R_1$ is phenyl or phenyl substituted with 1, 2, or 3 groups selected from $C_1$–$C_4$ alkyl and $C_1$–$C_4$ alkoxy.

27. A formulation of claim 24 employing a compound wherein $R_1$ is phenyl or phenyl substituted with 1, 2, or 3 groups selected from $C_1$–$C_4$ alkyl and $C_1$–$C_4$ alkoxy.

28. A formulation of claim 25 employing a compound wherein $R_1$ is phenyl or phenyl substituted with 1, 2, or 3 groups selected from $C_1$–$C_4$ alkyl and $C_1$–$C_4$ alkoxy.

29. A formulation of claim 26 wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

30. A formulation of claim 27 wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

31. A formulation of claim 28 wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

32. A method of treating hypercholesterolemia or atherosclerosis comprising administering to a mammal in need of such treatment an ACAT-inhibiting amount of a compound of claim 1.

33. A method of treating hypercholesterolemia or atherosclerosis comprising administering to a mammal in need of such treatment an ACAT-inhibiting amount of a compound of claim 7.

34. A method of treating hypercholesterolemia or atherosclerosis comprising administering to a mammal in need of such treatment an ACAT-inhibiting amount of a compound of claim 14.

35. A method according to claim 32 employing a compound wherein $R_1$ is phenyl or phenyl substituted with 1, 2, or 3 grouper selected from $C_1$–$C_4$ alkyl and $C_1$–$C_4$ alkoxy.

36. A method according to claim 33 employing a compound wherein $R_1$ is phenyl or phenyl substituted with 1, 2, or 3 groups selected from $C_1$–$C_4$ alkyl and $C_1$–$C_4$ alkoxy.

37. A method according to claim 34 employing a compound wherein $R_1$ is phenyl or phenyl substituted with 1, 2, or 3 groups selected from $C_1$–$C_4$ alkyl and $C_1$–$C_4$ alkoxy.

38. A method according to claim 35 employing a compound wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

39. A method according to claim 36 employing a compound wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

40. A method according to claim 37 employing a compound wherein $R_5$ is $C_8$–$C_{20}$ alkyl, phenyl, or phenyl substituted with 1, 2, or 3 groups selected from $C_1$–$C_4$ alkyl and $C_1$–$C_4$ alkoxy.

* * * * *

UNITED STATES PATENT AND TRADEMARK OFFICE
CERTIFICATE OF CORRECTION

PATENT NO. : 5,491,170
DATED : February 13, 1996
INVENTOR(S) : Helen Tsenwhei Lee et al.

It is certified that error appears in the above-indentified patent and that said Letters Patent is hereby corrected as shown below:

Column 22, line 62, "phenol" should read -- phenyl --.

Column 23, line 28, "claim 4" should read -- claim 3 --.

Column 24, line 47, after "trifluoromethyl" insert -- COOH --.

Column 26, line 39, "claim 15" should read -- claim 14 --.

Signed and Sealed this

Twenty-seventh Day of March, 2001

Attest:

NICHOLAS P. GODICI

Attesting Officer

Acting Director of the United States Patent and Trademark Office